United States Patent [19]
Donahoe et al.

[11] Patent Number: 5,198,420
[45] Date of Patent: Mar. 30, 1993

[54] USE OF MULLERIAN INHIBITING SUBSTANCE AND ITS AGONISTS AND ANTAGONISTS IN THE TREATMENT OF RESPIRATORY DISTRESS SYNDROME

[75] Inventors: Patricia K. Donahoe, Weston; Elizabeth A. Catlin, Newton, both of Mass.

[73] Assignee: The General Hospital Corporation, Boston, Mass.

[21] Appl. No.: 913,789

[22] Filed: Jun. 30, 1992

Related U.S. Application Data

[63] Continuation of Ser. No. 416,235, Oct. 2, 1989, abandoned.

[51] Int. Cl.$^5$ .................. A61K 37/04; A61K 37/02
[52] U.S. Cl. .................. 424/85.8; 514/12; 514/13; 514/8; 530/397; 530/387.2; 530/388.24; 530/389.2
[58] Field of Search ............... 514/8, 12, 13; 530/387, 530/397

[56] References Cited

PUBLICATIONS

Catlin, E. A. et al., *Am J. Obstet. Gynecol.* 159: 1299–1303 (1988).
Catterton, W. Z. et al., *Pediatr. Res.* 13:104–108 (1979).
Coughlin, J. P. et al., *Mol. Cell Endocrinol.* 49:75–86 (1987).
Hutson, J. M. et al., *Endocrinology*, 113:1470–1475 (1983).
Hutson, J. M. et al., *Science*, 223:586–589 (1984).
Nielsen, H. C. et al., *J. Clin. Invest.*, 69:611–616 (1982).
Nielsen, H. C. *Am. Rev. Respir. Dis.*, 137:275 (1988).
Odom, M. J. et al., *Endocrinology*, 113:1470–1475 (1983).
Pepinsky, R. B. et al., *J. Biol. Chem.*, 263:18961–18964 (1988).
Post, M. et al., *J. Biol. Chem.*, 261:2179–2184 (1986).
Rooney, S. A. et al., *Biochim. Biophys. Acta.*, 450:121–130 (1976).
Snyder, J. M. et al., *Cell Tissue Res.*, 220:17–25 (1981).
Sundell, H. W. et al., *Am. J. Pathol.*, 100:707–726 (1980).
Torday, J. S. et al., *Am. Rev. Respir. Dis.*, 123:205–208 (1981).
Torday, J. S. et al., Biochim. Biophys Acta., 835:23–28 (1985).
Ueno, S. et al., *Endocrinology*, 128:1652–1659 (1988).
Whitsett, J. A. et al., *J. Biol. Chem.*, 262:7908–7913 (1987).

*Primary Examiner*—Merrell C. Cashion, Jr.
*Assistant Examiner*—Choon P. Koh
*Attorney, Agent, or Firm*—Sterne, Kessler, Goldstein & Fox

[57] ABSTRACT

The use of agonists or antagonists of Mullerian Inhibiting Substance to suppress or treat respiratory distress syndrom. The treatment can be accomplished by providing an effective amount of the agonist or antagonist to a neonatal or prenatal individual.

9 Claims, 3 Drawing Sheets

USE OF MULLERIAN INHIBITING SUBSTANCE AND ITS AGONISTS AND ANTAGONISTS IN THE TREATMENT OF RESPIRATORY DISTRESS SYNDROME

This invention was made with Government support under CA 17393 awarded by NIH. The Government has certain rights in the invention.

This application is a continuation of application Ser. No. 07/416,235, filed Oct. 2, 1989, now abandoned.

FIELD OF THE INVENTION

The present invention pertains to the use of Mullerian Inhibiting Substance in the treatment of respiratory distress syndrome and related diseases.

BACKGROUND OF THE INVENTION

I. Mullerian Inhibiting Substance

Mullerian Inhibiting Substance (MIS) is a 140 kd glycoprotein responsible for the regression of the Mullerian duct in a male embryo (Jost, A., *Comotes Rend. Soc. Biol.*, 140:463–464 (1946); Jost, A., *Comotes Rend. Soc. Biol.*, 141:135–136 (1947); Balanchard, M. G., et al., *Ped. Res.*, 8:968–971 (1974); Donahoe, P. K., et al., *Biol. Repro.*, 15:329–334 (1976); Donahoe, P. K., et al., *J. Ped. Surg.*, 12:323–330 (1977); Donahoe, P. K., et al., *Biol. Reoro.*, 16:238–243 (1977)).

Mullerian Inhibiting Substance has been found to be a glycoprotein hormone. The substance is produced by fetal and neonatal Sertoli cells of the testes. MIS has been partially purified and found to be a dimeric glycoprotein of 72,000 and 74,000 daltons (Budzik, G. P., et al in: Lash, J. W., et al. (eds.) *Develop Mental Mechanisms: Normal and Abnormal.* Alan R. Liss, NY pp. 207–223 (1985)). The purification of MIS is described in Donahoe, P. K., et al., U.S. Pat. Nos. 4,404,188 and 4,510,131 (both herein incorporated by reference).

Monoclonal antibodies to MIS have been developed (Mudgett-Hunter, M., *J. Immunol.* 128:1327 (1982)) and found to be useful in the purification and preparation of MIS (Shima, H., et al., *Hybridoma.* 3:201–214 (1984); Donahoe, P. K., et al., U.S. Pat. No. 4,487,833 (herein incorporated by reference), and in the immunohistochemical detection of MIS in the Sertoli cells of the testes ((Hayashi, M., et al., *J. Histochem. Cytochem.*, 32:649–654 (1984)), and in the granulosa cells of the ovaries (Takahasi, M. et al., *Biol. Reoro.* 35:447 (1986)). Using these monoclonal antibodies, a radioimmunoassay has been developed to detect MIS (Necklaws, E. C., et al., *Endocrinol.*, 118:791–796 (1986)). This radioimmunoassay has detected MIS in the follicular fluid of mature bovine ovaries (Vigier, B., et al., *Endocrinol.*, 114:1315–1320 (1984)), in fluid from the large and small follicles of new born ovaries (Necklaws, E. C., et al., *Endocrinol.*, 2:791–796 (1986)), and in incubation media of bovine granulocyte cells (Vigier, B., et al., *Endocrinol.*, 114:1315–1320 (1984)).

MIS has been found to be cytotoxic to human ovarian cancer cells in vitro (Donahoe, P. K., et al., *Science.* 205:913–915 (1979)). It has also been found to be effective against this cancer in vivo (Donahoe, P. K., et al., U.S. Pat. No. 4,510,131, herein incorporated by reference). MIS has also been found to be an effective contraceptive agent (International Patent Application W088/00054, herein incorporated by reference).

II. Respiratory Distress Syndrome

Neonatal respiratory distress syndrome ("RDS") is an important cause of infant morbidity and mortality. Newborn males develop RDS more frequently and experience greater disease severity than females. This correlation may reflect the fact that fetal pulmonary maturity in human males lags behind females by 1.2 to 2.5 weeks (Torday, J. S. et al., *Am. Rev. Respir. Dis.* 123:205–208 (1981)). The functional lung immaturity of RDS is characterized by insufficient pulmonary surfactant, a mixture of phospholipids and proteins synthesized in alveolar type II pneumocytes (Avery, M. E. et al., *Am. J. Dis. Child* 97:517–523 (1959), Bleasdale, J. E., et al. In: *Pulmonary Development: Transition from Intrauterine to Extrauterine Life,* Nelson G. H., ed. New York: Marcel Dekker, Inc. 47–73 (1985), which references are incorporated herein by reference).

Premature birth is associated with most cases of RDS, but the etiology of the male disadvantage in RDS is unclear. Biochemical and morphological differentiation of the fetal lung is a complex process governed by cell-cell interactions, by a variety of hormones, messengers, and molecular substrates (Bleasdale, J. E., et al. In: *Pulmonary Development: Transition from Intrauterine to Extrauterine Life,* Nelson G. H., ed. New York: Marcel Dekker, Inc. 47–73 (1985), Rooney, S. A., et al., *Am. Rev. Respir. Dis.* 131:439–460 (1985), Masters, J. R. W., et al., *Devel. Biol* 51:98–108 (1976), Bernfield, M. R., et al., *The Role of Extracellular Matrix in Development.* New York, Alan R. Liss, Inc. 545–572 (1984), which references are incorporated herein by reference), and by many as yet undefined stimulatory and inhibitory factors. That inhibitory factors are important in fetal lung development is suggested by the precocious differentiation of type II cells that occurs when human fetal lung is explanted in vitro (Snyder, J. M. et al., *Cell Tissue Res.* 220:17–25 (1981)).

SUMMARY OF THE INVENTION

Male neonates develop respiratory distress syndrome (RDS) with a greater incidence and mortality than do females; the cause of this male disadvantage remains obscure. Male fetuses are exposed to higher levels of androgens and Mullerian Inhibiting Substance (MIS). Androgens have been shown to inhibit fetal lung maturation and recent evidence in vitro indicates that MIS, a Sertoli cell derived glycoprotein made early in ontogeny of the testis, may also inhibit lung development. The role of MIS in respiratory distress syndrome was determined by studying the ability of MIS to inhibit maturation of the fetal lung in vivo.

Human recombinant MIS was injected into fetal rats, and the serum levels of recombinant MIS were measured using an enzyme-linked immunosorbent assay. Fetal lung tissue was histologically analyzed for protein, glycogen, DNA, and disaturated phosphatidylcholine content. Peak serum levels of recombinant MIS were measured at 6 hours, with an apparent elimination half-life of 3 hours, and without leakage into adjacent littermates injected with vehicle alone. Female fetal rat lung tissue exposed to recombinant Mullerian Inhibiting Substance ($10^{-9}$M, $10^{-8}$M) revealed depressed disaturated phosphatidylcholine content both 48 and 72 hours after injection, compared with female vehicle injected littermates. Male lungs of the same gestational age appeared inhibited at a higher ($10^{-8}$M) recombinant MIS dose. These inhibitory effects indicate that MIS, as well as androgens, plays a causative or important ancillary role in the sexual dimorphism which characterizes the neonatal respiratory distress syndrome.

In detail, the present invention thus concerns a method of treatment for respiratory distress syndrome comprising the administration, to an individual in need of such treatment, of an effective amount of either (1) an agonist of MIS, such as MIS itself, or (2) an antagonist of MIS, such as EGF, an antibody capable of binding to MIS, or a fragment of an antibody, which fragment is capable of binding to MIS. MIS itself, preferably in high, continuous doses may thus be used therapeutically (for example, to down-regulate the MIS receptor).

The invention additionally concerns the above methods wherein the individual is a newborn human, or wherein the individual is a fetus, and the agonist or antagonist is administered to the mother of the fetus prior to the birth of the fetus.

The invention additionally concerns the above methods wherein the agonist or antagonist is administered intravenously, intramuscularly, subcutaneously, enterally, or parenterally.

DESCRIPTION OF THE PREFERRED EMBODIMENTS

I. Role of MIS in Respiratory Distress Syndrome

Two testis-derived hormones have been found to be produced beginning early in embryogenesis by fetal males, Mullerian Inhibiting Substance (MIS) and testosterone. The mechanism of MIS action is discussed by Donahoe, P. K. et al., *Rec. Prog. Horm. Res.* 43:431–468 (1987), which reference is incorporated herein by reference.

Dihydrotestosterone, a testosterone derivative, has been shown to inhibit type II pneumocyte differentiation in vitro and in vivo (Nielsen, H. C. et al., *J. Clin. Invest.* 69:611–616 (1982), Torday, J. S., et al. *Biochim. Biophys. Acta.* 835:23–28 (1985)), as assessed by synthesis of disaturated phosphatidylcholine ("DSPC"), the major glycerophospholipid of pulmonary surfactant and the primary surfaceactive component.

As indicated above, Mullerian Inhibiting Substance is a potent glycoprotein essential for normal fetal male sexual development. MIS undergoes proteolytic cleavage to produce a transforming growth factor-beta-like fragment (Pepinsky, R. B. et al., *J. Biol. Chem.* 263:18961–18964 (1988), which reference is incorporated herein by reference). Both bovine MIS and recombinantly produced human MIS, in nanomolar to $10^{-11}$ molar concentrations, have been shown to inhibit DSPC accumulation in female fetal rat lung cultures (Catlin, E. A., et al. *Am. J. Obstet. Gynecol.* 159(5):1299–1303 (1988), Catlin, E. A., et al., *Amer. Rev. Respirat. Dis.* 139:A197 (1989), Catlin, E. A., et al., *Amer. Rev. Respirat. Dis.* 137:19 (1988), which references are incorporated herein by reference). The present invention is based, in part, on the discovery that MIS contributes to the male disadvantage in neonatal respiratory distress syndrome by inhibiting fetal lung maturation.

Mullerian Inhibiting Substance is elaborated in the human male by fetal Sertoli cells in the testis after week 6 of gestation. It interacts with the urogenital ridge, initiating a mesenchymal-epithelial interaction that culminates in eradication of the epithelial Mullerian duct and its mesenchyme (Trelstad, R. L., et al., *Dev. Biol.* 92:27–40 (1982)); MIS action is likely mediated via a specific membrane receptor. In addition to these paracrine effects, MIS is known to exist as a circulating hormone, earlier demonstrated in the chick-quail chimera (Hutson, J. M., et al., *Endocrinology* 113:1470–1475 (1983), which reference is incorporated herein by reference), now measurable in premature and term neonatal human male serum. MIS levels in males at birth are 40–70 nanograms/ml, approximately $0.29$–$0.5 \times 10^{-9}$M (Hudson, P. L., et al., *J. Clin. Endocrinol. Metab.* (1989)). MIS can also be detected in the ovaries of adult rats (Ueno, S. et al., *Endocrinol.* 125:1060–1066 (1989), which reference is incorporated herein by reference). It is known to have an antiproliferative effect on several gynoceological tumor cell lines (Wallen, J. W. et al., *Cancer Res.* 49:2005–2011 (1989), which reference is incorporated herein by reference).

The high MIS levels measured in serum of newborn males, taken together with the present in vivo and previous in vitro (Catlin, E. A., et al. *Am. J. Obstet. Gynecol.* 159(5):1299–1303 (1988)) lung studies, indicate that MIS plays a regulatory role in fetal lung maturation.

While testosterone derived dihydrotestosterone also suppresses lung maturation (Nielsen, H. C. et al., *J. Clin. Invest.* 69:6-11–616 (1982), Torday, J. S., et al. *Biochim. Biophys. Acta.* 835:23–28 (1985), which references are incorporated herein by reference), fetal levels of testosterone decline throughout the third trimester reaching concentrations of $68.1 \pm 59.5$ nanograms/100 ml (i.e. $0.68 \pm 0.59$ nanograms/ml) in males and $12.0 \pm 6.0$ nanograms/100 ml (i.e. $0.12 \pm 0.06$ nanograms/ml) in females ($2.36 \pm 0.42 \times 10^{-9}$M) shortly after birth (Forest, M. G., et al., *J. Clin. Endocrinol. Metab.* 36:1132-1142 (1973), Griffin, J. E., et al., In: *Williams Textbook of Endocrinology*, Wilson, J. D. et al., eds. 7th ed., W. B. Saunders, Philadelphia, 1985, pages 259-311). Premature males, the babies at highest risk for development of the newborn respiratory distress syndrome, often have high plasma concentrations of testosterone. Since testosterone also enhances the biological activity of MIS in vitro and in vivo (Ikawa, H., et al., *J. Pediatr. Surg.* 17(5):453-458 (1982)), the fetal lung inhibitory effects of these 2 male hormones, alone and in synergy, provide a potential rationale for the so-called male disadvantage in neonatal respiratory distress syndrome. Another possible mechanism for MIS mediated lung effect could be interruption of so-called stress-induced lung maturation; this explanation is consonant with the female data but the significant stimulation measured 48 hours after injection with rMIS followed by a relative inhibition in male lungs may not as easily support this idea, unless the concept of down regulation, caused by exposure to endogenous or exogenous MIS is considered.

Although the mechanism(s) by which MIS exerts its effects in fetal lung has not yet been fully ascertained, the presently available information permits one to identify appropriate MIS antagonists for usein the present invention. It has been reported that MIS inhibits membrane phosphorylation in a cell-line richly endowed with EGF (Epidermal Growth Factor) receptors (A431), by decreasing autophosphorylation of these receptors (Coughlin, J. P., et al., *Mol. Cell Endocrinol.* 49:75-86 (1987), which reference is incorporated herein by reference). Conversely, EGF blocks MIS effect in a dose-dependent fashion in the MIS urogenital ridge bioassay and in an oocyte meiosis assay (Hutson, J. M., et al., *Science* 223:586-589 (1984), Ueno, S., et al., *Endocrinology* 123:1652-1659 (1988), which references are incorporated herein by reference). Because EGF has well described stimulatory effects on fetal lung development, including late gestation stimulation of type II epithelial cell differentiation with stimulation of phosphatidylcholine synthesis (Catterton, W. Z., et al., *Pediatr. Res.* 13:104-108 (1979), Sundell, H. W., et al., *Am. J. Pathol.* 100:707-726 (1980), Keller, G. H., et al., *Arch. Biochem. Biophys.* 211:321-326 (1981)), and because MIS and EGF seem to represent a natural antagonistic dyad in several model systems, it is conceivable that MIS could exert a regulatory effect on the fetal lung by blocking EGF receptor mediated membrane phosphorylation.

Based on the aggregate of in vitro and in vivo data in fetal lung, MIS has been found to be an inhibitory and possibly bifunctional regulator of fetal lung development. MIS, as well as androgens, may contribute to the sexual dimorphism seen in the neonatal respiratory distress syndrome. An understanding of the mechanism by which MIS regulates lung maturation in the fetus is of value in the treatment of infants ill with, and fetuses at risk for, respiratory distress syndrome.

II. The Molecules of the Present Invention

The present invention thus concerns a therapeutic treatment for respiratory distress syndrome comprising the administration of a pharmaceutical composition containing an either an agonist or an antagonist of MIS.

As used herein, the term "agonist" is intended to refer to an agent which increases the physiologic response of an organ or organism to the presence of a second agent. As demonstrated by Crowley et al., it is possible for an agonist of a hormone to suppress the physiologic effect of that hormone by, for example, down-regulating the expression of activity of the hormone (Crowley, W. F. et al., *New Engl. J. Med.* 309:1286-1290 (1983); Rudlin, C. R. et al., *Pediat. Res.* 19:192A (1985); Rudlin, C. R. et al., *Pediat. Res.* 19:633 (1985); Boepple, P. A. et al., *Endocr. Rew.* 7:24-33 (1986); Boeppel, P. A. et al., *Amer. J. Physiol.* 255:E559-E566 (1988); Klibanski, A. et al., *J. Clin. Endocrinol. Metab.* 68: 81-86 (1989), all of which references are incorporated herein by reference). Thus, MIS itself, as well as its functional derivatives may be provided as agonists to recipients in order to treat respiratory distress syndrome in accordance with the present invention. Preferably, when administered for this purpose, such agonists will be provided at elevated doses and/or for prolonged periods. Administration may be either pulsatile, or continuous during such periods.

In addition to the above-described agonists, anti-idiotypic antibodies to the MIS receptor, or to anti-MIS antibodies may be employed as agonists in accordance with the methods of the invention. Anti-idiotypic antibodies to the MIS receptor are preferably prepared using the method of Taylor, L. A. et al., "Development of an anti-idiotypic antibody as a probe for the Mullerian Inhibiting Substance (MIS) Receptor" In: *Growth Inhibitory and Cytotoxic Polypeptides.* Alan R. Liss, Inc., NY, pages 155-168 (1989), which reference is incorporated herein by reference. Antibodies to MIS may be obtained in the manner described by Ueno, S. et al., *Endocrinol.* 124:1000-1006 (1989), which reference is incorporated herein by reference. Other methods of obtaining antibodies are discussed below. In addition to intact anti-idiotypic antibodies, it is possible to employ fragments of such antibodies having the ability to bind to MIS receptor molecules, or to anti-MIS antisera.

As used herein, the term "antagonist" is intended to refer to an agent which diminishes the physiologic response of an organ or organism to the presence of a second agent. Thus, an antagonist of MIS would decrease the effectiveness of MIS by decreasing an individual's response to the presence of MIS. Similarly, an antagonist of EGF decreases the effectiveness of that agent. EGF is a preferred antagonist of MIS.

In accordance with the methods of the present invention, other suitable antagonists include antibodies capable of binding to MIS; fragments of antibodies having the ability to bind to MIS; functional derivatives of MIS having the ability to bind to MIS receptor molecules, but lacking other MIS activity; an MIS receptor molecule; functional derivatives of the MIS receptor molecule which have the ability to bind to MIS, etc.

Antibodies of value in the present invention may be obtained by introducing either the purified MIS molecules (or cells which naturally express these molecules) into an appropriate animal, as by intraperitoneal injection, etc. If desired, the serum of such an animal may be removed and used as a source of polyclonal antibodies capable of binding these molecules. It is, however, preferable to remove splenocytes from such animals, to fuse such spleen cells with a myeloma cell line and to permit such fusion cells to form a hybridoma cell which secretes monoclonal antibodies capable of binding MIS.

The hybridoma cells, obtained in the manner described above may be screened as described above to identify desired hybridoma cells that secrete antibody capable of binding to MIS.

Since such antibodies have the capacity to bind to MIS, they (and their fragments having antigen binding ability, such as Fab, F(ab)$_2$, etc.) may be used to attenuate respiratory distress syndrome, and thus provide an additional example of an agent which may be used in accordance with the present invention to treat this syndrome.

As indicated above, both polyclonal and monoclonal antibodies may be employed in accordance with the present invention. Of special interest to the present invention are antibodies to MIS (or their functional derivatives), which are produced in humans, or are "humanized" (i.e. non-immunogenic in a human) by recombinant or other technology. Humanized antibodies may be produced, for example by replacing an immunogenic portion of an antibody with a corresponding, but non-immunogenic portion (i.e. chimeric antibodies) (Robinson, R. R. et al., International Patent Publication PCT/US86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023; Better, M. et al., *Science* 240:1041-1043 (1988); Liu, A. Y. et al., *Proc. Natl. Acad. Sci. USA* 84:3439-3443 (1987); Liu, A. Y. et al., *J. Immunol.* 139:3521-3526 (1987); Sun, L. K. et al., *Proc. Natl. Acad. Sci. USA* 84:214-218 (1987); Nishimura, Y. et al, *Canc. Res.* 47:999-1005 (1987); Wood, C. R. et al., *Nature* 314:446-449 (1985); Shaw et al., *J. Natl. Cancer Inst.* 80:1553-1559 (1988), which references are incorporated herein by reference).

General reviews of "humanized" chimeric antibodies are provided by Morrison, S. L. (*Science.* 229:1202-1207 (1985)) and by Oi, V. T. et al., *BioTechniques* 4:214 (1986)).

Suitable "humanized" antibodies can be alternatively produced by CDR or CEA substitution (Jones, P. T. et al., *Nature* 321:552-525 (1986); Verhoeyan et al., *Science* 239:1534 (1988); Beidler, C. B. et al., *J. Immunol.* 141:4053-4060 (1988), which references are incorporated herein by reference).

The preparations disclosed herein are said to be "substantially free of natural contaminants" if they are substantially free of materials with which they are normally and naturally found.

As used herein, a "functional derivative" of a molecule (such as MIS or an MIS antagonist) is a compound which posesses a biological activity (either functional or structural) that is substantially similar to a biological activity of that molecule. The term "functional derivatives" is intended to include the "fragments," "variants," "analogs," or "chemical derivatives" of a molecule.

A "fragment" of a molecule, is meant to refer to any polypeptide subset of the molecule. Fragments of MIS which have receptor binding activity, but which lack other MIS activity and which are soluble (i.e not membrane bound) are especially preferred.

A "variant" of a molecule is meant to refer to a molecule substantially similar in structure and function to either the entire molecule, or to a fragment thereof. A molecule is said to be "substantially similar" to another molecule if both molecules have substantially similar structures or if both molecules possess a similar biological activity. Thus, provided that two molecules possess a similar activity, they are considered variants as that term is used herein even if the structure of one of the molecules not found in the other, or if the sequence of amino acid residues is not identical.

An "analog" of a molecule is meant to refer to a molecule substantially similar in function to either the entire molecule or to a fragment thereof.

As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed in *Remington's Pharmaceutical Sciences* (1980). "Toxin-derivatized" molecules constitute a special class of "chemical derivatives." A "toxin-derivatized" molecule is a molecule (such as MIS or an antibody to an MIS receptor) which contains a toxin moiety. The binding of such a molecule to a cell brings the toxin moiety into close proximity with the cell and thereby promotes cell death. Any suitable toxin moiety may be employed; however, it is preferable to employ toxins such as, for example, the ricin toxin, the diphtheria toxin, radioisotopic toxins, membrane-channel-forming toxins, etc. Procedures for coupling such moieties to a molecule are well known in the art.

As indicated above, one class of MIS antagonists of value in the present invention comprises functional derivatives of MIS which are able to bind to the MIS receptor, but which lack the lung impairing affect of MIS. The therapeutic advantages of such molecules may be augmented through the use of such functional derivatives of MIS which possess additional amino acid residues added to enhance coupling to carrier or to enhance their activity. Such molecules may lack certain amino acid residues, or may contain additional amino acid residues, so long as such derivatives exhibit the capacity to affect a symptom or characteristic of respiratory distress syndrome. Especially included are MIS derivatives which may lack (or contain) one or two or three (additional) amino acid residues from either their amino or carboxyl termini.

In addition to the above-described antibodies and antibody fragments, it is possible to employ anti-idiotypic antibodies (or their fragments) which bind to the MIS receptor, as antagonists of MIS in the treatment of respiratory distress syndrome. Methods of preparing such molecules are discussed above.

The molecules of the present invention may be obtained either synthetically, through the use of recombinant DNA technology, by proteolysis, or by other suitable means. A preferred method for the production of recombinant MIS is described by Epstein, J. et al., *In Vitro Cell. Dev. Biol.* 25:213-216 (1989), which reference is incorporated herein by reference)

III. Pharmaceutically Useful Compositions of the Present Invention

The molecules of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in Remington's Pharmaceutical Sciences (16th ed., Osol, A., Ed., Mack, Easton Pa. (1980)). In order to form a pharmaceutically acceptable composition suitable for effective administration, such compositions will contain an effective amount of the MIS molecule, or one of its functional derivatives, or agonists, together with a suitable amount of carrier vehicle.

Additional pharmaceutical methods may be employed to control the duration of action. Control release preparations may be achieved through the use of polymers to complex or absorb MIS, or its functional derivatives, or agonists. The controlled delivery may be exercised by selecting appropriate macromolecules (for example polyesters, polyamino acids, polyvinyl, pyrrolidone, ethylenevinylacetate, methylcellulose, carboxymethylcellulose, or protamine, sulfate) and the concentration of macromolecules as well as the methods of incorporation in order to control release. Another possible method to control the duration of action by controlled release preparations is to incorporate MIS molecules, or their functional derivatives, or agonists, into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatine-microcapsules and poly(methylmethacylate) microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

The compositions of the present invention may be prepared as articles of manufacture, such as "kits." Preferably, such kits will contain two or more containers which are specially adapted to receive MIS or one or more of its functional derivatives, and agonists.

IV. Administration of the Molecules of the Present Invention

The therapeutic effects of the compounds of the present invention may be obtained by providing to a patient any of the above molecules, either singly, or in combination with one another. As used herein, two agents are said to be co-administered when they are provided to tissue or to an individual in such close proximity of time that both agents can be observed to exert a detectable effect on the tissue or individual at the same time.

A composition is said to be "pharmacologically acceptable" if its administration can be tolerated by a recipient patient. Such an agent is said to be physiologically significant if its presence results in a detectable change in the physiology of a recipient patient.

In providing any of the agents of the present invention to a recipient patient, the dosage of administered agent will vary depending upon such factors as the patient's age, weight, height, sex, general medical condition, previous medical history, etc. In general, when providing any of the molecules of the present invention to a patient, it is preferable to administer such molecules in a dosage which ranges from about 1 pg/kg to 10 mg/kg (body weight of patient) although a lower or higher dosage may also be administered. Such molecules may be administered to patients intravenously, intramuscularly, subcutaneously, enterally, or parenterally. When administering such compounds by injection, the administration may be by continuous infusion, or by single or multiple boluses. Such compounds may also be provided by perfusion techniques. Such perfusion may be either systemic (as by introducing the compound to a recipient in a manner so as to cause it to be generally present throughout all or most of the organs or tissue of the recipient) or localized (as by bathing, injecting or perfusing such compounds into an isolated organ, tissue or region).

The compounds of the present invention are intended to be provided to recipient subjects in an "effective amount." An amount of a compound is said to be "effective" if, with regard to the treatment of respiratory distress syndrome, the dosage, route of administration, etc. of the compound is sufficient to suppress or prevent a symptom of respiratory distress syndrome. As used herein, an agent is said to be able to treat respiratory distress syndrome if, when administered to a patient, the agent is capable of either preventing, suppressing or attenuating the severity, extent or duration of a symptom of respiratory distress syndrome.

The administration of such compounds may be for either a "prophylactic" or "therapeutic" purpose. When provided prophylactically to suppress respiratory distress syndrome, the compounds are provided in advance of the detection of any symptom of respiratory distress syndrome. The prophylactic administration of the compounds serve to prevent or attenuate an anticipated or potential respiratory distress syndrome symptom. When provided therapeutically to suppress respiratory distress syndrome, the compounds are provided at (or shortly after) the detection of a symptom of respiratory distress syndrome. The therapeutic administration of the compounds serve to attenuate such actual condition. The compounds of the present invention may, thus, be provided either prior to the onset of respiratory distress syndrome (so as to suppress an anticipated symptom of this condition) or after the actual detection of a present symptom of respiratory distress syndrome.

The compounds of the present invention may be provided to a newborn patient at risk of developing respiratory distress syndrome, or to an individual actually experiencing a symptom of this disease. The compounds of the present invention may, alternatively, be provided to the mother of an unborn fetus (prior to the birth or parturition of the fetus) in order to suppress the possibility that the fetus (when born) will experience respiratory distress syndrome. When administered in this manner, the compound is provided to the unborn fetus via the mother's circulatory system, etc.). In yet another embodiment, the agents of the present invention may be administered to such a fetus directly (as by intrauterine injection, perfusion, etc.)

Having now generally described the invention, the same will be more readily understood through reference to the following examples which are provided by way of illustration, and are not intended to be limiting of the present invention, unless specified.

EXAMPLE 1

METHODS

Figure 1:
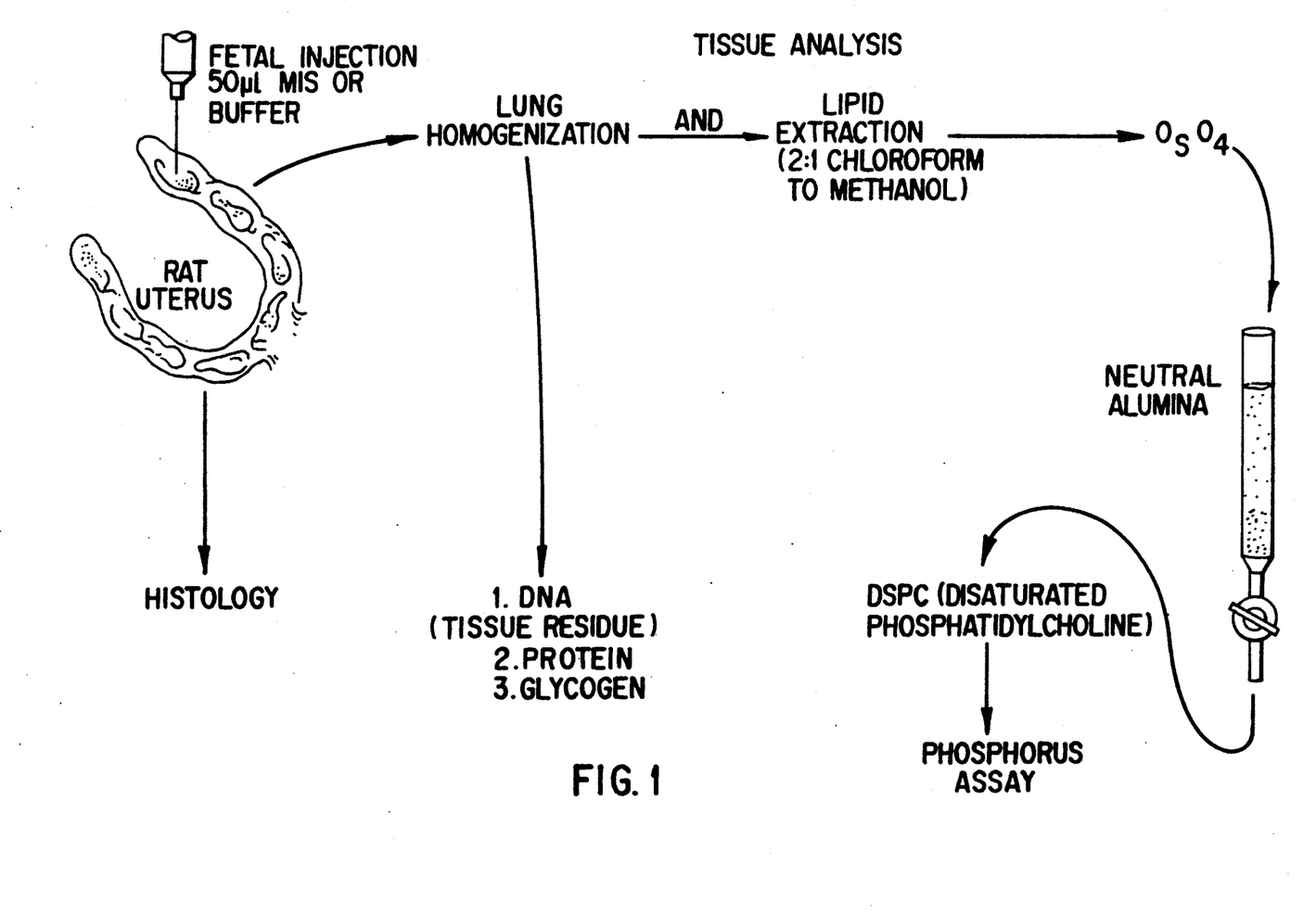
FIG. 1 shows the method of fetal administration of recombinant Mullerian Inhibiting Substance (MIS) or vehicle buffer and processing of lung tissue. Alternating fetuses within each litter received a single parenteral dose of MIS or vehicle buffer. 48 and 72 hours later, lungs were removed and analyzed for DSPC, DNA, glycogen, and protein content as well as processed for histologic examination.

Sprague-Dawley, Holtzman strain, time-pregnant rat dams were obtained from Holtzman Laboratories, (Madison, Wis.). Recombinant MIS was administered by transuterine injection to the fetus in vivo (FIG. 1), using a technique previously successful in producing fetal hyperinsulinemia (Catlin, E. A., et al., *Metabolism*

34:1110–1114 (1985), which reference is incorporated herein by reference). Rat dams, anesthetized with ether, underwent sterile laparotomy at 19.5 days gestation just prior to the late-gestation acceleration in DSPC accumulation in fetal rat lung (Funkhouser, J. D., et al., Biochim. Biophys. Acta. 530:9–16 (1978), which reference is incorporated herein by reference).

Alternate littermates were injected through the maternal uterus beneath their dorsal skin with 50 microliters of vehicle buffer or recombinant human Mullerian Inhibiting Substance ("rMIS"), producing a visible subcutaneous bleb. The animals of one additional litter were injected with vehicle buffer only. The uterus with injected fetuses was returned to its normal position and the mothers returned to their cages.

Forty-eight or 72 hours after fetal injection, fetuses were surgically delivered to avoid lung inflation and fetal sex was determined by direct inspection of gonads. Lungs were rapidly removed under a dissecting microscope, washed in ice-cold phosphate-buffered saline, and frozen at $-80°$ C. until analysis for DNA (Zamenhof, S., et al., J. Neurochem 19:61–68 (1972)), glycogen (Lo S, et al., J. Appl., Physiol. 28(2):234–236 (1970)), protein (Lowry, O. H., et al., J.- Biol. Chem. 193:265–275 (1951)), and DSPC (Folch, J., et al., J. Biol., Chem. 226:497–509 (1957), Mason, R. J., et al., J. Lipid Res. 17:281–284 (1976), Bartlett, et al., J. Biol. Chem. 234:466–468 (1959)). All of the above references are incorporated herein by reference.

Fetal lungs from several non-injected litters were also analyzed to provide normative data. Representative specimens were fixed, cut, and stained with hematoxylin and eosin. At the time of processing, lung tissue was thawed, weighed, and homogenized; crude lipid, extracted with chloroform: methanol, was reacted with osmium (Folch, J., et al., J. Biol. Chem. 226:497–509 (1957), Mason, R. J., et al., J. Lipid Res. 17:281–284 (1976)) from which the disaturated phosphatidylcholine (DSPC) was eluted with 7M ammonium hydroxide in chloroform and methanol, then ashed for phosphorus content (Bartlett, et al., J. Biol. Chem. 234:466–468 (1959)). Tracer amounts of dipalmitoyl phosphatidylcholine labeled with carbon 14 were added before chromatography in several experiments to estimate DSPC recovery which was routinely $\geq 90\%$.

EXAMPLE 2

MIS ELISA

To verify delivery and to determine fetal clearance of recombinant MIS, fetal serum was assayed by an enzyme-linked immunosorbent assay (ELISA) specific for human MIS (Hudson, P. L., et al., J. Clin. Endocrinol. Metab. (1989), U.S. patent application Ser. No. 07/299,158, which references are incorporated herein by reference), at intervals following transuterine injection.

In brief, an anti-human MIS monoclonal antibody obtained by cell fusion was first applied to wells, following by blocking buffer (female fetal bovine serum) to which samples and standards were added. Polyclonal antibody (rabbit) to MIS was next added and the resulting complex visualized with mouse anti-rabbit horseradish peroxidase. This ELISA is sensitive to human MIS concentrations in the 10 picomolar range.

EXAMPLE 3

PREPARATION OF MIS

Human MIS is a dimeric 140 kd glycoprotein which can now be produced recombinantly by transfected eukaryotic cells. Oligonucleotide probes were constructed using protein sequences from tryptic digests of the 70 and 74 kd proteins eluted from electrophoresis gels of reduced, purified bovine MIS. Degenerate oligonucleotide probes were used to screen a λgt10 cDNA library made from RNA of newborn bovine testis and the MIS bovine cDNA's identified. A human cosmid library was then screened using the bovine MIS cDNA to identify a genomic human MIS clone. A linear construct of the human MIS gene was then co-transfected with the dihydrofolate reductase gene, expressed in Chinese hamster ovary (CHO) cells, and amplified by methotrexate selection (Cate, R. L., et al., Cell 45:685–698 (1986), which reference is incorporated herein by reference). MIS produced by CHO cells can be purified from conditioned media by conventional chromatography (Budzik, G. P., et al., Cell 34:307–314 (1983), which reference is incorporated herein by reference) or by immunoaffinity chromatography using monoclonal antibodies directed against recombinant MIS (Shima, H., et al., Hybridoma 3:201–214 (1984), Pepinsky, R. B., et al., J. Biol. Chem. 263:18961–18964 (1988), which reference are incorporated herein by reference).

The human recombinant MIS preparations used in the in vivo experiments of the present invention were immunoaffinity purified by applying CHO media, concentrated by ultrafiltration, to a column of Affigel-10 agarose resin (BioRad) with immobilized monoclonal anti-human rMIS antibody. The rMIS was then chaotropically eluted with 2M ammonium thiocyanate and immediately desalted on a Sephadex G-25 column (Pepinsky, R. B., et al., J., Biol. Chem. 263:18961–18964 (1988)). Biologic potency of each rMIS preparation was assessed by an established organ culture assay that grades regression of 14.5 day female fetal rat urogenital ridges (Donahoe, P. K., et al., J. Surg. Res. 23:141–148 (1977), which reference is incorporated herein by reference) and by immunoreactivity quantitation by ELISA (Hudson, P. L., et al., J. Clin. Endocrinol. Metab., (1989), U.S. patent application Ser. No. 07/299,158).

Recombinant MIS preparations were run electrophoretically on reduced SDS polyacrylamide gels to establish the predominance of bands at 70 and 55 kd with the predicted amino terminal sequence of human MIS (Cate, R. L., et al., Cell 45:685–698 (1986), Pepinsky, R.B., et al., J. Biol. Chem. 263:18961–18964 (1988)). Each rMIS preparation also underwent western blot analysis using a polyclonal antibody to MIS; bands which cross blotted with the polyclonal antibody represented 95% of the preparations (Hudson, P. L., et al., J. Clin. Endocrinol. Metab. (1989)).

After initial experiments, protein content of the multiple rMIS preparations used ranged from 540–650 micrograms per ml, with rMIS ELISA levels of 113–360 micrograms/ml, which at 1/80 dilutions caused a 4–5+ (5+ =maximal) regression of the Mullerian duct in the organ culture bioassay (Donahoe, P. K., et al., J. Surg. Res. 23:141–148 (1977)).

Purified rMIS and its vehicle buffer (G-25 buffer: 0.02M HEPES, 0.15M NaCl, 10% glucose, pH 7.4) were similarly diluted sixteen fold in USP injection grade saline without preservative and sterilized prior to injection of 50 microliter volumes to achieve a dose of 5 to $7.9\times10^{-9}$M MIS, assuming equilibration in the 1 milliliter total body water of each fetus. The log high dose ($3\times10^{-8}$M) of rMIS or G-25 buffer was prepared using a 1 to 1 dilution in USP injection grade sterile water and a 70 microliter injection volume. Calculated estimates of osmolarities of delivered preparations ranged from 220-390 mOsm.

EXAMPLE 4

EFFECT OF MIS ON FETAL LUNGS IN VIVO

Six hours following subcutaneous fetal injection of 5 to $7.9\times10^{-9}$ molar rMIS (approximately 1 microgram of rMIS protein), serum levels of MIS were measured. Data was analyzed using CLINFO software (BBN, Cambridge, Mass., 1986) on a VAX/VMS mainframe. The null hypothesis was tested using Wilcoxon Rank Sum tests because data distribution was non-parametric. Significance was assigned for p values less than 0.05. Standard error of the mean is used to represent data dispersion in the descriptive statistics.

Figure 2:
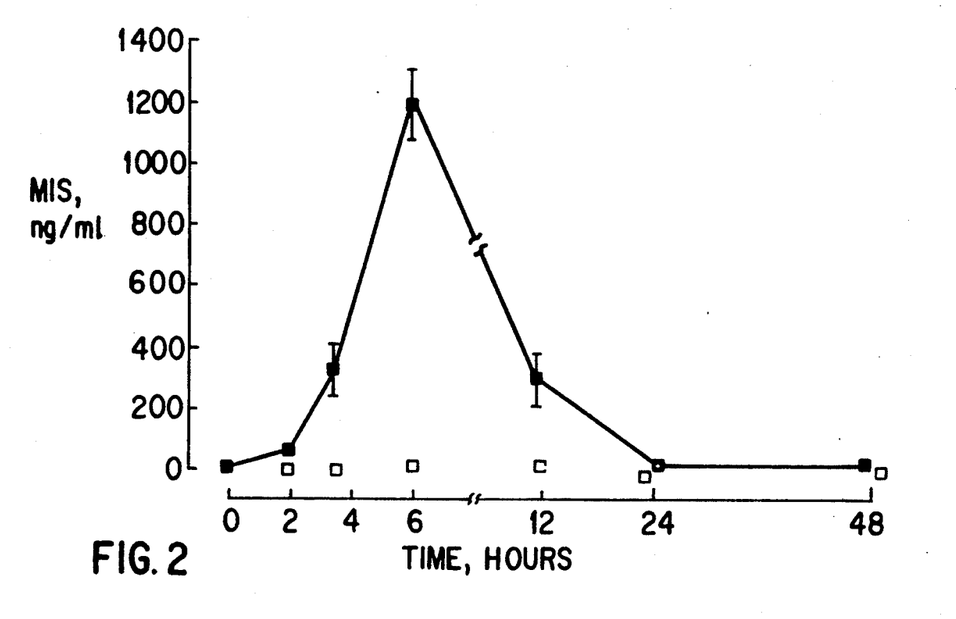
FIG. 2 shows fetal rat absorption and clearance of recombinant human MIS, 5 to $7.9 \times 10^{-9}$M, (approximately 1000 nanograms of MIS protein), following subcutaneous fetal injection in an isotonic aqueous vehicle. MIS injected, n=48; vehicle injected, n=44. Each data point represents the mean serum concentration of MIS in nanograms per milliliter ± the standard error of the mean (MIS, closed boxes; buffer, open boxes). Serum was assayed by an enzyme-linked immunosorbent assay (ELISA) specific for human MIS, sensitive to MIS concentrations in the 10 picomolar range.

At that time, 1,184 nanograms of MIS per milliliter of serum was observed. This value represented approximately 100% recovery of MIS assuming equilibration in the total body water of each fetus (FIG. 2). Fetal injection was well tolerated and mortality was negligible. Peak serum levels of rMIS, delivered in an aqueous relatively isotonic vehicle, were measured at 6 hours, with an apparent elimination halflife of 3 hours, and with no measurable leakage into adjacent vehicle injected littermates.

Figure 3A:
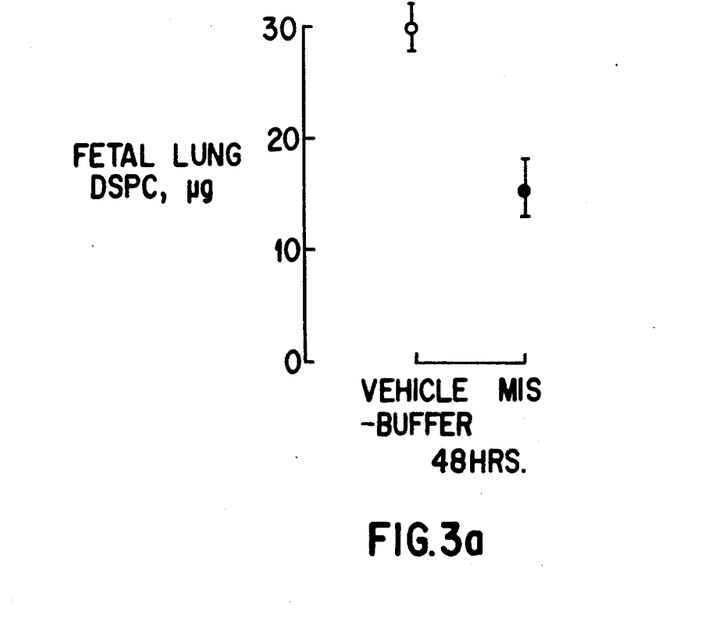
FIGS. 3A and 3B show female fetal lung disaturated phosphatidylcholine (DSPC) content 48 or 72 hours following a single parenteral dose of recombinant human MIS (rMIS) or vehicle buffer. Each point represents the mean ± the standard error of whole lung DSPC content. 3A) The lungs of female fetuses (n=13) injected with a $10^{-9}$M dose of rMIS when compared with those injected with buffer alone show, after 48 hours, a significant DSPC suppression with rMIS exposure, $p<0.05$. 3B) After 72 hours of exposure, the lungs of 14 rMIS injected ($10^{-9}$M, $10^{-8}$M) female fetuses compared to 16 female fetuses injected with buffer show persistent significant inhibition of DSPC accumulation following injection of rMIS compared to buffer, $p<0.05$.
Figure 3B:
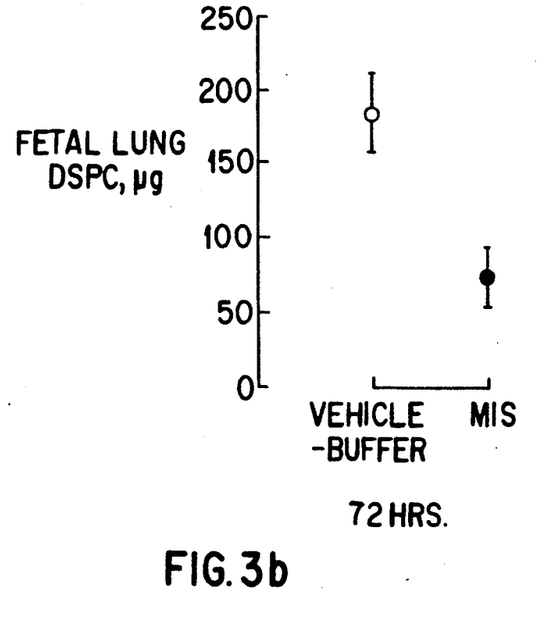

Lung tissue harvested from the female fetuses showed significant suppression of disaturated phosphatidylcholine (DSPC) content both 48 and 72 hours after a single dose of rMIS delivered to alternate fetuses in each litter (FIG. 3). This inhibition of biochemical maturation in lungs of female fetuses treated in vivo with human recombinant MIS was similar to that obtained when 17.5 day gestation female fetal lungs were incubated in vitro with either bovine MIS or human recombinant MIS (Catlin, E. A., et al. *Am. J. Obstet. Gynecol.* 159(5):1299-1303 (1988)). Other parameters of female fetal lung growth (protein, glycogen contents) were not affected by exposure to in vivo rMIS except that female lung DNA content was suppressed with $10^{-9}$M MIS but not with $10^{-8}$M MIS. The significance of this depression is not obvious, particularly since the higher rMIS dose did not similarly affect DNA levels in these females.

Analysis of male fetal lung tissue 72 hours after transuterine injection of rMIS revealed significant elevation in glycogen content ($p<0.01$, Table 1); glycogen depletion, commonly used as a measure of maturation in fetal rat lung, coincides with both accumulation of surfactant-containing lamellar bodies and increasing DSPC content (Williams, M. C., et al., *Am. Rev. Respir. Dis.* 115:37-47 (1977), which reference is incorporated herein by reference).

In Table 1, 19.5 day fetuses were injected subcutaneously with $10^{-9}$M and $10^{-8}$M recombinant Mullerian Inhibiting Substance or vehicle. 72 hours later lung tissue was analyzed for DSPC, DNA, protein, and glycogen content. Values represent mean±standard error of the mean; *$p<0.05$, +$p<0.01$. Inhibition of DSPC accumulation in female fetuses was seen following rMIS administration. Elevation in lung glycogen content as well as a relative DSPC/DNA inhibition suggests a modified inhibition by exogenous MIS in fetal males.

The lower DSPC content measured in rMIS exposed males after 72 hours, compared to vehicle controls (Table 1), did not reach statistical significance, however, at the higher dose of rMIS ($10^{-8}$M), DNA synthesis was stimulated and analysis of DSPC/DNA revealed relative inhibition of DSPC in treated males. Therefore, the elevated lung glycogen combined with the depressed DSPC/DNA values indicate that rMIS also inhibits fetal male lung development. Male lung tissue analyzed 48 hours after parenteral injection with a $10^{-9}$M dose of rMIS revealed stimulation of DSPC content (vehicle controls=9.88 µg±2.03, rMIS treated subjects=28.11 µg±4.3, $p<0.05$), in contrast to the suppression at 48 and 72 hours measured in females and the 72 hour findings in males. Both rMIS treated and control fetal lung specimens had normal, non-toxic cellular architecture, and alveolar ducts, connective tissue septae and subepithelial capillaries typical of the terminal saccular phase of fetal lung development, without consistent histologic differences in the dosage ranges tested.

Surgical manipulation is known to accelerate fetal lung maturation (Rooney, S. A., *Biophys. Biochim. Acta* 450:121-130 (1976)); this was confirmed when lung DSPC values from non-injected fetuses (n=10) on day 22.5 of gestation were compared with buffer injected fetuses (n TM 34): males=31.2±6.46 µg versus 141.94±20.4 µg, females=22 63±3.4 µg versus 180.83±25.72 µg. No statistical differences were found between the lungs of uninjected male and female lungs or between buffer injected male and female lungs. There was, as anticipated, a marked difference between the injected and non-injected fetuses, regardless of sex.

TABLE 1

| | FETAL LUNG AT 72 HOURS | | | |
|---|---|---|---|---|
| Sex, type of Treatment (n) | Protein (mg) | DNA (µg) | Glycogen (µg) | DSPC (µg) |
| Female, buffer (16) | 10.72 ± 1.09 | 999.1 ± 82.64 | 275.51 ± 45.71 | 180.83 ± 25.72 |
| Female, MIS (14) | 8.24 ± 0.56 | 816.5 ± 77.06 | 360.15 ± 84.41 | 89.01 ± 21.41* |
| Male, buffer (18) | 10.46 ± 0.92 | 974.8 ± 65.65 | 191.48 ± 37.7 | 141.94 ± 20.4 |
| Male, MIS (14) | 9.85 ± 0.42 | 1059.4 ± 87.7 | 514.53 ± 89.8+ | 100.62 ± 18.75 |

EXAMPLE 5

THE ROLE OF MIS IN THE TREATMENT OF RESPIRATORY DISTRESS SYNDROME

Consistent in vitro and in vivo inhibition of biochemical lung maturation in females by Mullerian Inhibiting Substance, prepared from either natural bovine (Budzik, G. P., et al., *Cell* 34:307-314 (1983)) or human recombinant sources, indicated that the fetal lung is an MIS responsive organ.

These data also indicate the existence of an MIS receptor in fetal lung. This discovery is underscored by the finding that a single rMIS dose at nanomolar to $10^{-8}$M concentrations was able to produce an inhibition of DSPC synthesis that was measurable 72 hours later, particularly when apparent peak rMIS absorption occurred after 6 hours and was undetectable by ELISA after 24 hours. The relative rMIS induced DSPC inhibition after 72 hours measured in males with enhanced cellular proliferation supports the conclusion that MIS responsivity is similarly present in male fetal lung.

Cultured human fetal lung production of the major surfactantassociated protein, Mr ™ 35,000, is inhibited by transforming growth factor-beta, (TGF-B) (Whitsett, J. A., et al., *J. Biol. Chem.* 262(16):7908-7913 (1987)), a homologue of MIS. TGF-B has been shown also to signal differentiative function, as measured by fibroblast pneumonocyte factor production, in the fetal lung fibroblast (Nielsen, et al., *Am. Rev. Respir. Dis.* 137:275 (1988)). Since TGF-B does not cause regression of the Mullerian duct in the organ culture assay for MIS, nor does the MIS ELISA recognize TGF-B$_1$ or TGF-B$_2$ (Hudson P. L., et al., *J. Clin. Endocrinol. Metab.* (1989)), these observed effects in fetal lung following transuterine, parenteral MIS injection appear to be MIS specific.

In comparison to females, the developing lungs of the male fetal rats treated in these experiments had been exposed to endogenous MIS from day 13.5 of gestation, when the testis first differentiates and is known to produce MIS, 6 days prior to the in vivo injection of rMIS on day 19.5 of gestation. Female fetuses prior to rMIS injection, in contrast, were exposed to little or no MIS. Endogenous circulating levels of MIS have not yet been measured in these younger rat fetuses, however, no MIS is detectable in serum from very premature human female babies whereas levels in male human fetuses are quite high (Hudson, P. L., et al., *J. Clin. Endocrinol. Metab.*). Prior male fetal rat MIS exposure may influence pulmonary cellular differentiation, or down regulate MIS receptors, complicating the interpretation of the responses of males exposed to exogenous rMIS.

Since glucocorticoids, a known stimulator of fetal pulmonary surfactant synthesis (Post, M., et al., *J. Biol. Chem.* 261:2179-2184 (1986), Liggins, et al., *J. Endocrinol.* 45:515-523 (1969)), produce biphasic, concentration-dependent maturational responses when administered to cultured fetal lung (i.e., stimulation with $10^{-9}$, $10^{-10}$M concentrations and inhibition at $10^{-8}$, $10^{-7}$M levels (Odom, M. J., et al., *Endocrinology* 123(4):1712-1720 (1988)), the bimodal responses in males and unimodal inhibition in females to rMIS seem to be physiologically consistent, and appear to represent sex-specific and concentration-dependent fetal lung effects.

Although the foregoing refers to particular preferred embodiments, it will be understood that the present invention is not so limited. It will occur to those ordinarily skilled in the art that various modifications may be made to the disclosed embodiments and that such modifications are intended to be within the scope of the present invention.

What is claimed is:

1. A method of treating respiratory distress syndrome comprising administering, to an individual in need of such treatment, an effective amount of an antagonist of MIS selected from the group consisting of an antibody capable of binding to MIS, or a fragment of an antibody, which fragment is capable of binding to MIS.

2. A method of treating respiratory distress syndrome comprising administering, to an individual in need of such treatment, an effective amount of an antagonist of MIS selected from the group consisting of MIS, an anti-idiotypic antibody to the MIS receptor or a fragment of an anti-idiotypic antibody to the MIS receptor, which fragment is capable of binding the MIS receptor.

3. The method of claim 1, wherein said individual is a newborn human.

4. The method of claim 2, wherein said individual is a newborn human.

5. The method of claim 1, wherein said individual is a fetus, and wherein said antagonist is administered to the mother of said fetus prior to the birth of said fetus.

6. The method of claim 2, wherein said individual is a fetus, and wherein said antagonist is administered to the mother of said fetus prior to the birth of said fetus.

7. The method of claim 1, wherein said antagonist is administered intravenously, intramuscularly, subcutaneously, enterally, or parenterally.

8. The method of claim 2, wherein said antagonist is administered intravenously, intramuscularly, subcutaneously, enterally, or parenterally.

9. The method of claim 1, wherein said antibody is a monoclonal antibody.

* * * * *

UNITED STATES PATENT AND TRADEMARK OFFICE
CERTIFICATE OF CORRECTION

PATENT NO. : 5,198,420
DATED : March 30, 1993
INVENTOR(S) : Patricia DONAHOE et al.

It is certified that error appears in the above-identified patent and that said Letters Patent is hereby corrected as shown below:

| Column | Line | |
|---|---|---|
| 16 | 30 | "antagonist" should read --agonist--. |
| | 43 | "antagonist" should read --agonist--. |
| | 48 | "antagonist" should read --agonist--. |

Signed and Sealed this

Twenty-eighth Day of December, 1993

Attest:

BRUCE LEHMAN

Attesting Officer

Commissioner of Patents and Trademarks